United States Patent
Wallis et al.

(10) Patent No.: US 11,454,620 B2
(45) Date of Patent: Sep. 27, 2022

(54) METHOD FOR COMPREHENSIVE EVALUATION OF INDOOR ENVIRONMENTAL QUALITY

(71) Applicant: Gigabase Environmental Consulting (Shanghai) Co., Ltd, Shanghai (CN)

(72) Inventors: Raefer Keith Wallis, Shanghai (CN); Le Yin, Shanghai (CN); Xiang Jun Xu, Shanghai (CN)

(73) Assignee: Gigabase Environmental Consulting (Shanghai) Co., Ltd, Shanghai (CN)

( * ) Notice: Subject to any disclaimer, the term of this patent is extended or adjusted under 35 U.S.C. 154(b) by 760 days.

(21) Appl. No.: 16/338,723

(22) PCT Filed: Jan. 24, 2017

(86) PCT No.: PCT/CN2017/072442
§ 371 (c)(1),
(2) Date: Apr. 2, 2019

(87) PCT Pub. No.: WO2018/107563
PCT Pub. Date: Jun. 21, 2018

(65) Prior Publication Data
US 2020/0124580 A1 Apr. 23, 2020

(30) Foreign Application Priority Data
Dec. 13, 2016 (CN) .......................... 201611145038.3

(51) Int. Cl.
*G01N 33/00* (2006.01)
*F24F 11/30* (2018.01)
*F24F 11/62* (2018.01)

(52) U.S. Cl.
CPC .......... *G01N 33/0004* (2013.01); *F24F 11/30* (2018.01); *F24F 11/62* (2018.01)

(58) Field of Classification Search
CPC ........ G01N 33/0004; F24F 11/30; F24F 11/62
See application file for complete search history.

(56) References Cited

FOREIGN PATENT DOCUMENTS

| CN | 103323567 A | 9/2013 |
|---|---|---|
| CN | 104198657 A | 12/2014 |

(Continued)

*Primary Examiner* — Jamel E Williams
(74) *Attorney, Agent, or Firm* — Edwin A. Sisson, Attorney at Law, LLC; Jeffrey J. Banyas

(57) ABSTRACT

The present invention provides a method for comprehensively assessing indoor environmental quality. Pollutant concentration data used in the method is an average value calculated after sampling is performed at a plurality of positions in an indoor space, and is therefore relatively accurate, so that an excessively high or excessively low pollutant concentration at a position is prevented from impairing the accuracy of a measurement result. In the method, concentrations of pollutants are further converted into damage values, the damage values of the pollutants are converted into a total damage value based on a predetermined rule, and an air index is then calculated according to the total damage value, where the calculated air index reflects the impact of various pollutants on air healthiness. Therefore, by using the method for comprehensively assessing indoor environmental quality of the present invention, the measurement is precise, and indoor air healthiness can be comprehensively reflected.

8 Claims, 1 Drawing Sheet

(56) References Cited

FOREIGN PATENT DOCUMENTS

| | | | | |
|---|---|---|---|---|
| CN | 105868215 A | * | 8/2016 | |
| KR | 20160073754 A | | 6/2016 | |
| WO | WO-2006094252 A2 | * | 9/2006 | ............. G06Q 50/12 |

* cited by examiner

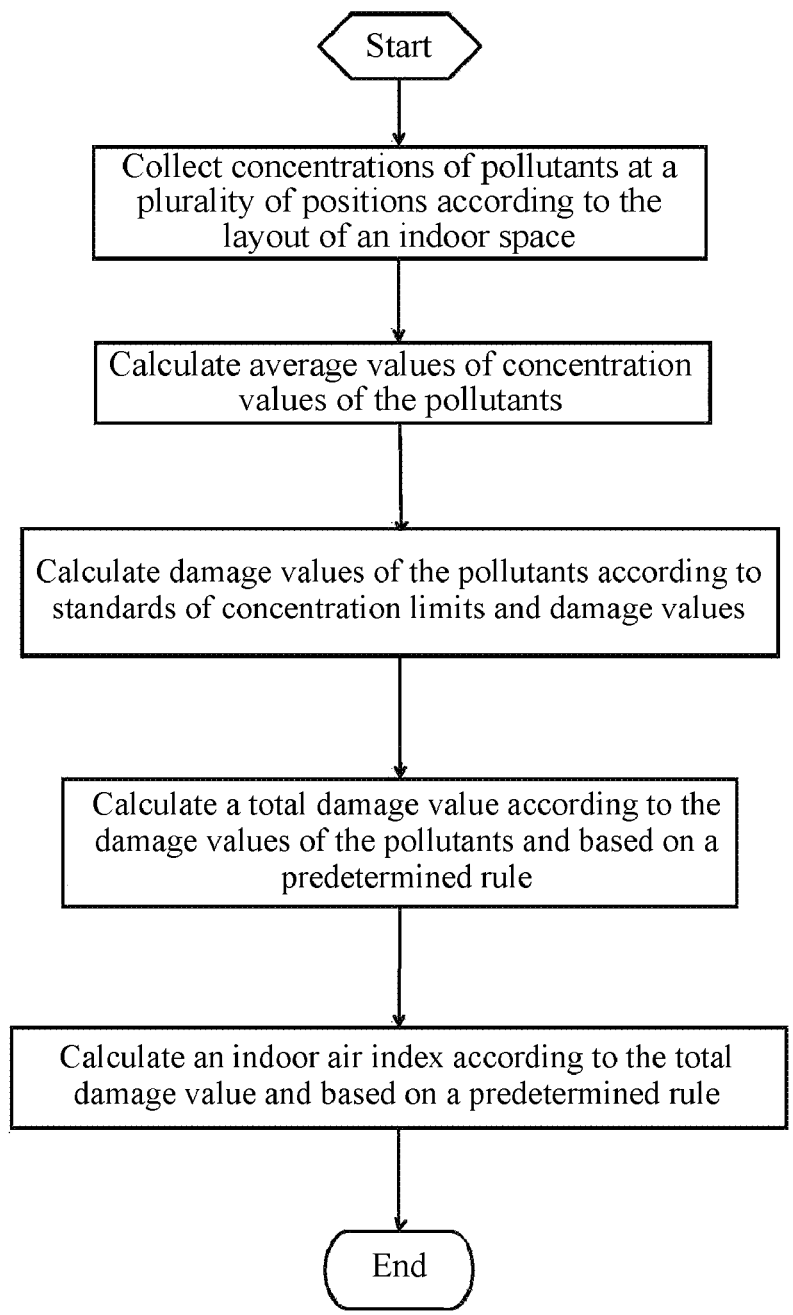

METHOD FOR COMPREHENSIVE EVALUATION OF INDOOR ENVIRONMENTAL QUALITY

PRIORITIES AND CROSS REFERENCES

This Application claims priority from International Application No. PCT/CN2017/072442 filed on 24 Jan. 2017 and Chinese Application No. 201611145038.3 filed on 13 Dec. 2016 the teachings of each of which are incorporated by reference herein in their entirety.

BACKGROUND

Technical Field

The present invention relates to the field of environmental pollution prevention and control, and in particular, to a method for comprehensively assessing indoor environmental quality used to assess indoor air quality.

Related Art

Environmental quality directly affects people's health. Air is one of the three most important things that sustain life. China is currently faced with a severe air pollution problem. People are concerned with air quality on a daily basis. People stay indoors most of the time and therefore have more concern for indoor air quality.

However, air in an indoor space flows less freely than that in an outdoor space. Different regions have different traffic. An indoor space usually includes a plurality of sub-spaces between which air does not flow freely. Therefore, an air sample collected by an air monitor only reflects air quality in a small region around the air monitor but cannot fully reflect overall indoor air quality.

An air quality index (AQI) is a nonlinear dimensionless index that quantitatively describes air quality. The AQI is calculated according to concentrations of pollutants. At present, in a method for calculating air quality, air quality is mainly calculated according to concentrations of pollutants collected at environmental monitoring points and by using the following formula:

$$I_i = \frac{I_{high} - I_{low}}{C_{high} - C_{low}}(C_i - C_{low}) + I_{low}, \text{ and}$$

$$I = \max(I_1, I_2, I_3 \ldots I_n),$$

where $I_i$ denotes an individual air quality index corresponding to a pollutant i, $C_i$ denotes a concentration of the pollutant i, $C_{low}$ denotes a concentration limit less than or equal to C and is a constant, $C_{high}$ denotes a concentration limit greater than or equal to C and is a constant, $I_{low}$ denotes an index threshold corresponding to $C_{low}$ and is a constant, and $I_{high}$ denotes an index threshold corresponding to $C_{high}$ and is a constant.

Currently, in the used method for calculating air quality, an AQI only reflects the most severe pollutant but does not reflect the impact of other less severe pollutants on the AQI.

SUMMARY

The present invention is used to resolve the foregoing problem, and the objective is to provide a method for comprehensively assessing indoor environmental quality that achieves precise measurement and can comprehensively reflect indoor air healthiness.

The present invention provides a method for comprehensively assessing indoor environmental quality, including the following steps:

step 1: arranging a plurality of air monitors according to an indoor space, collecting air in the indoor space, and obtaining a plurality of groups of concentration values of pollutants;

step 2: obtaining a group of average concentration values of the pollutants according to all the groups of concentration values of the pollutants obtained in the step 1 and based on a predetermined rule;

step 3: calculating a total damage value according to the average concentration values of the pollutants obtained in the step 2 and based on a predetermined rule, including:
  step 3-1: setting standards of concentration limits of the pollutants and corresponding damage values,
  step 3-2: calculating damage values of the pollutants according to the standards, and
  step 3-3: calculating a total damage value according to the damage values of the pollutants and based on a predetermined rule; and step 4, calculating an indoor air index according to the total damage value and based on a predetermined rule.

Further, the method for comprehensively assessing indoor environmental quality provided in the present invention may further have the following feature: in the step 1, each air monitor combines a concentration value data flow within a period of time into one concentration value.

Further, the method for comprehensively assessing indoor environmental quality provided in the present invention may further have the following feature: in the step 1, the air monitor combines a concentration value data flow within a period of time by calculating a median or an average or by removing isolated points in the concentration value data flow and then calculating an average value.

Further, the method for comprehensively assessing indoor environmental quality provided in the present invention may further have the following feature: in the step 2, the group of average concentration values of the pollutants are obtained by calculating averages of all the groups of concentration values of the pollutants.

Further, the method for comprehensively assessing indoor environmental quality provided in the present invention may further have the following feature: in the step 2, the group of average concentration values of the pollutants are obtained by weighting and averaging all the groups of concentration values of the pollutants according to the area or traffic of a sub-space in which each air monitor is placed.

Further, the method for comprehensively assessing indoor environmental quality provided in the present invention may further have the following feature: in the step 3-2, a damage value of a single pollutant is obtained according to a concentration and by using a piecewise linear calculation method, and a calculation formula is as follows:

$$l_i = \frac{C_i - C_{low}}{C_{high} - C_{low}} \times (L^*_{high} - L^*_{low}) + L^*_{low},$$

where $l_i$ denotes a damage value of a pollutant, $C_i$ denotes a concentration of the pollutant, $C_{low}$ denotes a concentration limit less than or equal to $C_i$ and is a constant, $C_{high}$ denotes a concentration limit greater than or equal to $C_i$ and is a constant, $L_{high}^*$ denotes a damage value corresponding to the concentration limit greater than or equal to $C_i$, and $L_{low}^*$ denotes a damage value corresponding to the concentration limit less than or equal to $C_i$.

Further, the method for comprehensively assessing indoor environmental quality provided in the present invention may further have the following feature: in the step 3-3, the total damage value is calculated according to the damage values of the pollutants and by using a p-norm formula, where the p-norm formula is as follows:

$$l = (l_1, l_2, \ldots, l_i, \ldots, l_n), 1 \leq p < \infty, \text{ and}$$

$$L = \|l\|_p = \left(\sum_{i=1}^{n} |l_i|^p\right)^{1/p},$$

where L denotes the total damage value, $l_i$ denotes a damage value of a pollutant, and l denotes a vector generated from the damage values.

Further, the method for comprehensively assessing indoor environmental quality provided in the present invention may further have the following feature: the value of p is 2.

Further, the method for comprehensively assessing indoor environmental quality provided in the present invention may further have the following feature: in the step 4, air quality is calculated according to the total damage value and by using the following formula:

$$I = \frac{100 - L}{100},$$

where I denotes the air quality, and L denotes the total damage value; and the air quality is then converted into a percentage to obtain an air index.

The present invention provides the following advantages:

In the method for comprehensively assessing indoor environmental quality according to the present invention, an average value of each pollutant in an indoor space is calculated after sampling is performed at a plurality of positions in the indoor space, and an obtained pollutant concentration is relatively accurate, so that an excessively high or excessively low pollutant concentration at a position is prevented from impairing the accuracy of a measurement result. Concentrations of pollutants are converted into damage values, the damage values of the pollutants are converted into a total damage value based on a predetermined rule, and an air index is then calculated according to the total damage value, where the calculated air index reflects the impact of various pollutants on air healthiness. Therefore, by using the method for comprehensively assessing indoor environmental quality of the present invention, the measurement is precise, and indoor air healthiness can be comprehensively reflected.

BRIEF DESCRIPTION OF THE DRAWINGS

FIG. 1 is a flowchart of a method for comprehensively assessing indoor environmental quality according to an embodiment of the present invention.

DETAILED DESCRIPTION

To make the technical measures, inventive features, objectives, and effects of the implementations of the present invention more comprehensible, the method for comprehensively assessing indoor environmental quality of the present invention is described in detail in the following embodiments with reference to the accompanying drawings.

The method for comprehensively assessing indoor environmental quality is used to comprehensively assess indoor air quality, so as to reflect indoor air healthiness, so that people can grasp indoor air quality more intuitively.

As shown in FIG. 1, the method for comprehensively assessing indoor environmental quality includes the following steps.

Step S1: Arrange a plurality of air monitors according to an indoor space, collect air in the indoor space, and obtain a plurality of groups of concentration values of pollutants.

An indoor space is usually relatively large and is usually divided into a plurality of sub-spaces. Air monitors are arranged at several chosen points when a space is relatively large. When there are sub-spaces, an air monitor is placed in each sub-space. In this way, an excessively high or excessively low air pollutant concentration collected at a point can be prevented from impairing the accurate reflection of indoor air quality. Each air monitor obtains concentration values of a group of pollutants.

Each air monitor combines a concentration value data flow within a period of time into one concentration value. The air monitor combines a concentration value data flow within a period of time by calculating a median or an average or by removing isolated points in the concentration value data flow and then calculating an average value. In this way, occasional factors can be excluded.

In this embodiment, pollutants are categorized into three types, namely, $PM_{2.5}$, $CO_2$, total volatile organic compounds (TVOC). Concentration values of the three types of pollutants, namely, $PM_{2.5}$, $CO_2$, and TVOC are obtained from the air monitors.

Step S2: Obtain a group of average concentration values of the pollutants according to all the groups of concentration values of the pollutants obtained in step 1 and based on a predetermined rule.

A method for calculating an average concentration value of a pollutant may be as follows. The group of average concentration values of the pollutants are obtained by calculating averages of all the groups of concentration values of the pollutants. That is, an average value of concentration values of $PM_{2.5}$ that are obtained from all the air monitors is calculated, an average value of concentration values of $CO_2$ that are obtained from all the air monitors is calculated, and an average value of concentration values of TVOC that are obtained from all the air monitors is calculated.

Alternatively, a method for calculating an average concentration value of a pollutant may be as follows. The group of average concentration values of the pollutants are obtained by weighting and averaging all the groups of concentration values of the pollutants according to the area or traffic of a sub-space in which each air monitor is placed.

Step 3: Calculate a total damage value according to the average concentration values of the pollutants obtained in step 2 and based on a predetermined rule. Step 3 includes the following steps.

Step 3-1: Set standards of concentration limits of the pollutants and corresponding damage values, as shown in Table 1. Table 2, Table 3, and Table 4 show correspondences between concentration limits of single pollutants and corresponding damage values during specific calculation.

TABLE 1

Concentration limits of the pollutants and corresponding damage values

| L* | PM$_{2.5}$ (μg/m$^3$) | TVOC (μg/m$^3$) | CO$_2$ (ppm) |
|---|---|---|---|
| Completely damageless L* = 0 | 15 | 200 | 600 |
| Acceptable L* = 11.5 | 35 | 500 | 800 |
| Severely damageful L* = 100 | 120 | 1000 | 2500 |

TABLE 2

Concentration limits of PM$_{2.5}$ and corresponding damage values

| C$_{low}$ | C$_{high}$ | L$_{low}$* | L$_{high}$* |
|---|---|---|---|
| 0 | 15 | 0 | 0 |
| 15 | 35 | 0 | 11.5 |
| 35 | 120 | 11.5 | 100 |

TABLE 3

Concentration limits of TVOC and corresponding damage values

| C$_{low}$ | C$_{high}$ | L$_{low}$* | L$_{high}$* |
|---|---|---|---|
| 0 | 200 | 0 | 0 |
| 200 | 500 | 0 | 11.5 |
| 500 | 1000 | 11.5 | 100 |

TABLE 4

Concentration limits of CO$_2$ and corresponding damage values

| C$_{low}$ | C$_{high}$ | L$_{low}$* | L$_{high}$* |
|---|---|---|---|
| 0 | 600 | 0 | 0 |
| 600 | 800 | 0 | 11.5 |
| 800 | 2500 | 11.5 | 100 |

The total damage value is 100. Each pollutant has three breakpoint values that respectively correspond to "damageless" (damage value L*=0), "acceptable" (L*=11.5), and "severely damageful to health" (L*=100). Reference has been made to related research results for the selection of breakpoint values.

When the value of PM$_{2.5}$ exceeds 120 μg/m$^3$, the value of TVOC exceeds 1000 μg/m$^3$ or the value of CO$_2$ exceeds 2500 ppm in indoor air, the indoor air is severely polluted and is unsuitable for long stay of people. Moreover, generally, in an indoor environment, the values of PM$_{2.5}$, TVOC and CO$_2$ do not exceed such values.

Step 3-2: Calculate damage values of the pollutants according to the standards in Table 1, Table 2, Table 3, and Table 4.

A damage value of a single pollutant is obtained according to a concentration and by using a piecewise linear calculation method, and a calculation formula is as follows:

$$l_i = \frac{C_i - C_{low}}{C_{high} - C_{low}} \times (L^*_{high} - L^*_{low}) + L^*_{low},$$

where $l_i$ denotes a damage value of a pollutant, $C_i$ denotes a concentration of the pollutant, $C_{low}$ denotes a concentration limit less than or equal to $C_i$ and is a constant, $C_{high}$ denotes a concentration limit greater than or equal to $C_i$ and is a constant, $L_{high}^*$ denotes a damage value corresponding to the concentration limit greater than or equal to $C_i$, and $L_{low}^*$ denotes a damage value corresponding to the concentration limit less than or equal to $C_i$.

PM$_{2.5}$ is used as an example. When $C_{PM2.5} \leq 15$, $l_{PM2.5}=0$. When $15 < C_{PM2.5} \leq 35$, $$l_{PM2.5} = \frac{C_{PM2.5} - 15}{33 - 15} \times (11.5 - 0) + 0 = \frac{C_{PM2.5} - 15}{33 - 15} \times 11.5.$$

When $35 < C_{PM2.5} \leq 120$, $$l_{PM2.5} = \frac{C_{PM2.5} - 35}{120 - 35} \times (100 - 11.5) + 11.5.$$

When $120 \leq C_{PM2.5}$, $l_{PM2.5}=100$.

Step 3-3: Calculate a total damage value according to the damage values of the pollutants and based on a predetermined rule.

The total damage value is calculated according to the damage values of the pollutants and by using a p-norm formula. First, damage values of the pollutants obtained in the previous step are used to construct a vector ($l_{PM2.5}$, $l_{TVOC}$, $l_{CO2}$) in a space R$^n$. A norm is a function having a "length" concept. A length value of the vector may be obtained. The p-norm formula is as follows:

$$l = (l_1, l_2, \ldots, l_i, \ldots, l_n), 1 \leq p < \infty, \text{ and}$$

$$L = \|l\|_p = \left(\sum_{i=1}^{n} |l_i|^p\right)^{1/p},$$

where L denotes the total damage value, $l_i$ denotes a damage value of a pollutant, l denotes a vector generated from the damage values, and p is a constant. The value of p determines the contributions of damage values of different pollutants to the total damage value. When the value of p is smaller, the total damage value is closer to a sum of the damage values of the pollutants. When the value of p is larger, the total damage value is closer to the largest one of the damage values of the pollutants.

In Case A, only one pollutant has a damage value greater than 0. In this case, p is any value greater than 1, and the total damage value does not change.

When $1 \leq p < \infty$, the concentrations of the pollutants and the total damage value are shown in Table 5.

TABLE 5

Concentrations of the pollutants and the total damage value when $1 \leq p < \infty$

| PM$_{2.5}$ (μg/m$^3$) | TVOC (μg/m$^3$) | CO$_2$ (ppm) | L |
|---|---|---|---|
| 32 | 200 | 600 | 10 |

In Case B, at least two pollutants have damage values greater than 0. In this case, p has different values. When various pollutants have different concentrations, a same total damage value can be obtained.

When p=1.5, the concentrations of the pollutants and the total damage value are shown in Table 6.

TABLE 6

Concentrations of the pollutants and
the total damage value when p = 1.5

| $PM_{2.5}$ (µg/m³) | TVOC (µg/m³) | $CO_2$ (ppm) | L |
|---|---|---|---|
| 23 | 320 | 680 | 10 |

The concentrations of the pollutants and the total damage value are shown in Table 7 when p=2.

TABLE 7

Concentrations of the pollutants and
the total damage value when p = 2

| $PM_{2.5}$ (µg/m³) | TVOC (µg/m³) | $CO_2$ (ppm) | L |
|---|---|---|---|
| 25 | 350 | 700 | 10 |

When p=2.5, the concentrations of the pollutants and the total damage value are shown in Table 8.

TABLE 8

Concentrations of the pollutants and
the total damage value when p = 2.5

| $PM_{2.5}$ (µg/m³) | TVOC (µg/m³) | $CO_2$ (ppm) | L |
|---|---|---|---|
| 26 | 370 | 710 | 10 |

For Case A, Case B that apparently should be categorized into a same health grade is selected. A corresponding value of p is then chosen and used as a parameter in the P-norm formula. It is found out through research that during the calculation of an AQI, the most suitable value of p is 2.

Step S4: Calculate an indoor air index according to the total damage value and based on a predetermined rule.

Air quality is calculated according to the total damage value and by using the following formula:

$$I = \frac{100 - L}{100},$$

where I denotes the air quality, and L denotes the total damage value.

The calculated air quality is then converted into a percentage to obtain an air index. Compared with a score between 0 and 500 used in a current AQI, a percentage form is more easily comprehensible to people.

An air index calculated by using this patent is compared with an AQI obtained by using a calculation method from the United States Environmental Protection Agency, as shown in Table 9.

TABLE 9

Table of AQIs obtained by using the two methods

| $PM_{2.5}$ (µg/m³) | TVOC (µg/m³) | $CO_2$ (ppm) | Air index | AQI |
|---|---|---|---|---|
| 50 | 200 | 600 | 73% | 120 |
| 50 | 500 | 900 | 66% | 120 |

In Table 9, when the current method for calculating air quality is used, the AQI is 120 and is the same as that obtained by using this patent. The AQI only reflects the pollution severity of the major pollutant $PM_{2.5}$ but does not reflect the contributions of TVOC and $CO_2$ to air pollution. The air index obtained in this patent comprehensively reflects overall impact of various pollutants.

When the concentrations of all the pollutants are acceptable, if the concentrations of the pollutants increase, the air index decreases relatively slightly, and when the concentrations of all the pollutants are not acceptable, if the concentrations of the pollutants increase, the air index decreases relatively rapidly, as shown in Table 10 and Table 11.

TABLE 10

Air indices when the concentrations
of all the pollutants are acceptable

| $PM_{2.5}$ (µg/m³) | TVOC (µg/m³) | $CO_2$ (ppm) | Air index |
|---|---|---|---|
| 15 | 500 | 800 | 84% |
| 35 | 500 | 800 | 80% |

TABLE 11

Air indices when the concentrations of
all the pollutants are not acceptable

| $PM_{2.5}$ (µg/m³) | TVOC (µg/m³) | $CO_2$ (ppm) | Air index |
|---|---|---|---|
| 35 | 600 | 900 | 64% |
| 55 | 600 | 900 | 53% |

As can be seen from Table 10 and Table 11, when the concentration of $PM_{2.5}$ is increased by 20 µg/m³ in both Table 10 and Table 11, if the concentrations of all the pollutants are not acceptable, the AQI decreases more rapidly.

For a same air index, there may be different combinations of concentrations of pollutants. An air index reflects the impact of various pollutants on health, as shown in Table 12 and Table 13.

TABLE 12

Different combinations of concentrations
of pollutants when an air index is 90%

| $PM_{2.5}$ (µg/m³) | TVOC (µg/m³) | $CO_2$ (ppm) | Air index |
|---|---|---|---|
| 32 | 200 | 600 | 90% |
| 25 | 350 | 700 | 90% |

TABLE 13

Different combinations of concentrations
of pollutants when an air index is 80%

| $PM_{2.5}$ (µg/m³) | TVOC (µg/m³) | $CO_2$ (ppm) | Air index |
|---|---|---|---|
| 43 | 200 | 600 | 80% |
| 35 | 500 | 800 | 80% |

The foregoing implementations are preferred cases of the present invention and are not used to limit the protection scope of the present invention.

What is claimed is:

1. A method for comprehensively assessing indoor environmental quality, comprising the following steps:
   step 1: arranging a plurality of air monitors according to an indoor space, collecting air in the indoor space, and obtaining a plurality of groups of concentration values of pollutants;

step 2: obtaining a group of average concentration values of the pollutants according to all the groups of concentration values of the pollutants obtained in the step 1 and based on a predetermined rule;

step 3: calculating a total damage value according to the average concentration values of the pollutants obtained in the step 2 and based on a predetermined rule, comprising:

step 3-1: setting standards of concentration limits of the pollutants and corresponding damage values, step 3-2: calculating damage values of the pollutants according to the standards, and step 3-3: calculating a total damage value according to the damage values of the pollutants and based on a predetermined rule; and step 4: calculating an indoor air index according to the total damage value and based on a predetermined rule, wherein in the step 1, each air monitor combines a concentration value data flow within a period of time into one concentration value.

2. The method for comprehensively assessing indoor environmental quality according to claim 1, wherein in the step 1, the air monitor combines a concentration value data flow within a period of time by calculating a median or an average or by removing isolated points in the concentration value data flow and then calculating an average value.

3. The method for comprehensively assessing indoor environmental quality according to claim 1, wherein in the step 2, the group of average concentration values of the pollutants are obtained by calculating averages of all the groups of concentration values of the pollutants.

4. The method for comprehensively assessing indoor environmental quality according to claim 1, wherein in the step 2, the group of average concentration values of the pollutants are obtained by weighting and averaging all the groups of concentration values of the pollutants according to the area or traffic of a sub-space in which each air monitor is placed.

5. The method for comprehensively assessing indoor environmental quality according to claim 1, wherein in the step 3-2, a damage value of a single pollutant is obtained according to a concentration and by using a piecewise linear calculation method, and a calculation formula is as follows:

$$l_i = \frac{C_i - C_{low}}{C_{high} - C_{low}} \times (L_{high}^* - L_{low}^*) + L_{low}^*,$$

wherein $l_i$ denotes a damage value of a pollutant, $C_i$ denotes a concentration of the pollutant, $C_{low}$ denotes a concentration limit less than or equal to $C_i$ and is a constant, $C_{high}$ denotes a concentration limit greater than or equal to $C_i$ and is a constant, $L_{high}^*$ denotes a damage value corresponding to the concentration limit greater than or equal to $C_i$, and $L_{low}^*$ denotes a damage value corresponding to the concentration limit less than or equal to $C_i$.

6. The method for comprehensively assessing indoor environmental quality according to claim 1, wherein in the step 3-3, the total damage value is calculated according to the damage values of the pollutants and by using a p-norm formula, wherein the p-norm formula is as follows:

$$l = (l_1, l_2, \ldots, l_i, \ldots, l_n), 1 \le p < \infty, \text{ and}$$

$$L = \|l\|_p = \left(\sum_{i=1}^{n} |l_i|^p\right)^{1/p},$$

wherein L denotes the total damage value, $l_i$ denotes a damage value of a pollutant, and l denotes a vector generated from the damage values.

7. The method for comprehensively assessing indoor environmental quality according to claim 5, wherein the value of p is 2.

8. The method for comprehensively assessing indoor environmental quality according to claim 1, wherein in the step 4, air quality is calculated according to the total damage value and by using the following formula:

$$I = \frac{100 - L}{100},$$

wherein I denotes the air quality, and L denotes the total damage value; and the air quality is then converted into a percentage to obtain an air index.

* * * * *